United States Patent [19]

Johnson et al.

[11] Patent Number: 5,696,077
[45] Date of Patent: Dec. 9, 1997

[54] PHARMACEUTICAL COMPOSITION CONTAINING BOTULINUM B COMPLEX

[75] Inventors: Eric A. Johnson; Michael C. Goodnough, both of Madison, Wis.; Gary E. Borodic, Canton, Mass.

[73] Assignee: Associated Synapse Biologics, Cambridge, Mass.

[21] Appl. No.: 316,820

[22] Filed: Oct. 3, 1994

Related U.S. Application Data

[63] Continuation of Ser. No. 140,328, Oct. 20, 1993, abandoned.

[51] Int. Cl.$^6$ .......................... A61K 39/08; A61K 39/00; A61K 38/00; A61K 38/16
[52] U.S. Cl. ..................... 514/2; 424/184.1; 424/234.1; 424/247.1
[58] Field of Search ..................... 424/184.1, 234.1, 424/247.1; 514/2

[56] References Cited

U.S. PATENT DOCUMENTS 4,932,936  6/1990  Dykstra et al. .......................... 604/51

FOREIGN PATENT DOCUMENTS

| 0068607 | 6/1981 | Japan | 424/94.3 |
|---|---|---|---|
| 2059970 | 4/1981 | United Kingdom | 514/12 |
| WO 94/28922 | 12/1994 | WIPO . | |
| WO 94/28923 | 12/1994 | WIPO . | |

OTHER PUBLICATIONS

Schantz, E.J., et al., Journal of the Association of Official Analytical Chemists, vol. 61, pp. 96–99, Jan. 1978.
Melling et al., Eye, vol. 2, pp. 16–23, 1988; "*Clostridium Botulinum* Toxins: Nature and Preparation for Clinical Use".
Kozaki et al., Infection and Immunity, vol. 10, pp. 750–756, 1974; "Purification and Some Properties of Progenitor Toxins . . . ".
Borodic et al., Annals of Neurology, vol. 31, p. 113, Jan. 1992; "Treatment of Spasticity with Botulinum Toxin" (letter).
Schantz, E. J. et al., Microbiol. Rev., vol. 56, pp. 80–99, Mar. 1992; "Properties and Use of Botulinum Toxin . . . ".
Schwarz, W., Arch. Lebensmittelhyg., vol. 30, pp. 29–33, 1979; (abstract); "Examinations on the stability."
Memin, B. et al., Rev. Neurol. (France), vol. 148, pp. 212–214, 1992; (abstract); "Effects on botulinum toxin on spasticity".
Saprykina, T.P. et al., Zh. Mikrobiol. Epidemiol. Immunobiol., vol. 57, pp. 86–91, 1980; (abstract); "Obtaining homogenous . . . ".
Clarke, C.E., Q. J. Med., vol. 82, pp. 197–205, Mar. 1992; "Therapeutic Potential of Botulinum Toxin in Neurological . . . ".
Jankovic, J. et al., New Eng. J. Med., vol. 324, pp. 1186–1194, 1991; "Therapeutic Uses of Botulinum Toxin".
Das, T.K. et al., Postgrad. Med. J., vol. 65, pp. 208–210, 1989; "Effect of treatment with botulinum toxin . . . ".
Das, T.K. et al., Brit. J. Clin. Practice, vol. 43, pp. 401–403, 1989; "Botulinum toxin in treating spasticity".
Goodnough et al. Stabilization of botulinum toxin type A during lyophilization. Applied and Environmental Microbiology. 58(10):3426–3428, Oct. 1992.
BOTOX in Physician's Desk Reference. Ed. David W. Sifton, Medical Economics Data Production Company, Montvale, New Jersey, 1994.
Pikal, Michael J., "BioPharm", *Freeze–Drying of Proteins Part II: Formulation Selection*, 20–30 (Oct. 1990).
Evans et al., Eur. J. Biochem. 154, 409–416 (1986).
Patterson–Curtis et al., Applied & Environmental Microbiology, vol. 55, No. 6., Jun. 1989, pp. 1544–1548.
Sellin et al., Acta Physiol Scand, vol. 119, 1983, pp. 127–133.
Singh, et al., mOlecular and Cellular Biochemistry, vol., 1989 pp. 87–95.

*Primary Examiner*—Douglas W. Robinson
*Assistant Examiner*—Thanda Wai
*Attorney, Agent, or Firm*—Testa, Hurwitz & Thibeault, LLP

[57] ABSTRACT

A pharmaceutical preparation containing a complex consisting of type B botulinum neurotoxin and stabilizing proteins, both derived from *C. botulinum*, admixed with a pharmaceutically acceptable excipient is provided. The preparation is effective for inducing titratable, local, selective muscle denervation in a patient suffering from a disorder characterized by involuntary muscle spasm or contraction.

16 Claims, 3 Drawing Sheets

C. botulinum type B complex purification

High titer stock culture in cooked meat media or TPGY
↓
Inoculate 1 liter step-up culture of toxin production medium
Incubate at 37 degrees C overnight
↓
Inoculate 11 liter carboy with step-up culture
Incubate at 37 degrees C for 4-5 days
↓
Add 3N sulfuric acid to pH 3.5
Allow ppt to settle overnight
↓
Decant supernatant and collect ppt
Add:
1. distilled water to 2 liters
2. 150 ml of 1 M calcium chloride
3. 1 N sodium hydroxide to pH 6.5

→ Stir at room temp for 1-2 hrs
↓
Centrifuge and add 1 N HCl to supernatant to pH 3.7
↓
Collect ppt and dissolve in 50mM citrate, pH 5.5
↓
Centrifuge, apply and run supernatant on DEAE column equilibrated with same buffer
↓
Toxin complexes in unbound fraction may be further separated into L and M complexes with gel filtration (G200)

Note: typical yields are in the range of 10-20 mg of both complexes/l of culture

Fig. 3 ns the reversability of the inhibition of calcium-
PHARMACEUTICAL COMPOSITION CONTAINING BOTULINUM B COMPLEX This is a continuation of application Ser. No. 08/140,328 filed on Oct. 20, 1993, now abandoned.

BACKGROUND OF THE INVENTION

The invention relates to a pharmaceutical composition containing a neurotoxin derived from *C. botulinum* and methods of using it for selective, local denervation of muscles to treat disorders characterized by uncontrolled muscle activity.

Botulinum neurotoxins are produced by certain strains of the bacterial species *Clostridium botulinum*, *Clostridium baratii* and *Clostridium butyricum*. Hatheway in "Bacterial Sources of Clostridial Neurotoxins" *Botulinum Neurotoxin and Tetanus Toxin*, Simpson, LL(ed), Academic Press, San Diego (1989) classifies the toxins into seven serotypes, designated A through G. The botulinum neurotoxins comprise a family of pharmacologically similar toxins that block acetylcholine release from peripheral nerves. In sufficient doses, they can cause paralysis and death.

*Clostridium botulinum* (*C. botulinum*) is a species which occurs widely in nature and which is a rare cause of food poisoning (i.e., botulism) from preserved foods which were not properly sterilized before canning. There are seven main types of *C. botulinum* strains characterized by antigenically distinct but pharmacologically similar neurotoxins. These very potent neurotoxins can be neutralized only by the specific antitoxin.

Type A botulinum toxin is currently approved by the FDA for clinical treatment of certain hyperactive muscle disorders. When locally injected into a striated muscle, botulinum toxin has a series of pharmacologic effects, including denervating the muscle by blocking the release of acetylcholine, thereby diminishing the contractability of the muscle and inducing muscle atrophy. These effects last about 10 to 15 weeks, after which the muscle regains its contractability and atrophy is reversed. These effects, e.g., the temporary denervation and contractability, make botulinum toxin a useful treatment for regional movement disorders which are characterized by uncontrolled muscle spasms. Botulinum A toxin has been used to treat a number of segmental movement disorders, including blepharospasm, hemifacial spasm, spasmodic torticollis, spasmodic dysphonia and regional hand dystonias. Scott et al., *Arch. Ophthalmol.*, 103:347-350 (1985); Elston and Russell, *Br. Med. J.*, 290: 1857-1859 (1985); Dutton and Buckley, *Arch. Neurol.*, 43:380-382 (1986); Borodic and Cozzolino, *Plast. Reconstr. Surg.*, 83(3): 546-554 (1989); Borodic et al., *Ear Nose and Throat J.*, (67(12); 914 (1988); Jankovic and Orman, Neurology, 37:616-623 (1987); Gelb et al., *Neurology*, 39:80-84 (1989); Fletcher and Quinn, *Curr. Opin. Neurol. Neurosurg.*, 2:330-333 (1989); Ludlow et al., *Otolaryngol. Head Neck Surg.*, 101:122-131 (1990); and Dykstra et al. *J. Urol.*, 139:919-922 (1988).

The B serotype of the neurotoxin produced by *C. botulinum* is immunologically distinct from the type A toxin. Analysis of the partial amino acid sequence for A and B types revealed greater homologies between the primary and secondary structure of the heavy chains than of the light chains: the degree of structural homology between the A and B serotypes is about 20% for the light chains and 40% for the heavy chains. The cross-reactivity of type B toxin with antibodies to type A toxin is very low, and antibodies to type A toxin will not neutralize type B toxin in the mouse assay.

Electrophysiological studies have demonstrated that types A and B neurotoxins affect different steps in the neurotransmitter release process. Type B affects synchronization of quantal transmitter release whereas type A does not. Differences in the reversability of the inhibition of calcium-dependent release of neurotransmitters also exist. The introduction of calcium into nerve terminals using a calcium ionophore produces the release of transmitter from synaptosomes poisoned by type A more readily than from those poisoned by type B neurotoxin. Aminopyridine was more effective at reversing inhibition produced by type A neurotoxin at the neuromuscular junction. It has been demonstrated that microtubule-dissociating drugs were effective in blocking the inhibitory effects of type B toxin on neurotransmitter release and ineffective against type A toxin.

The effects of type B neurotoxin on neurotransmitter release were demonstrated in an animal study by L. S. Sellin et al. in *Acta Physiol. Scand.*, 119:127-133 (1983). They compared the effects of types A and B neurotoxin in rat hind limbs. They reported that doses of between 1 and 20 mouse $LD_{50}$ of type A toxin produced paralysis in the rat limb, but that doses of more than 1200 $LD_{50}$ of type B toxin were needed to produced the same effect. They further reported that the effects of type B neurotoxin lasted only a few days, compared to two weeks for type A crystalline toxin.

Although type A neurotoxin has successfully been used to treat a number of muscular spastic disorders, it cannot be used on all afflicted patients. Some patients have become immune to type A botulinum toxin and produce antibodies against it thereby reducing its effectiveness. The literature contains reports of production of antibodies against type A toxin in some patients treated with the toxin, e.g., Tsui et al., *Ann.Neurol.*, 23:181 (1988); Brin et al., *Mov. Disord.*, 2:237 (1991). Antibodies have been shown to neutralize the beneficial effect of botulinum toxin. Tsui et al., ibid. The long term effects of repeated doses of type A toxin over many years is not clear, however, alternatives to type A toxin for treatment of muscle spastic disorders are needed.

SUMMARY OF THE INVENTION

The invention relates to a pharmaceutical preparation which is effective for inducing selective, local, titratable muscle denervation in a patient. The preparation comprises a protein complex containing *C. botulinum*, e.g., type B neurotoxin associated with non-toxic botulinum-derived proteins. The complex has a molecular weight in excess of about 300 kilodaltons (KD), preferably from about 300 to about 450 KD, as determined by gel filtration chromatography. The complex is admixed with an excipient which helps to maintain the stability of the complex during and after dilution to usable dosage units. The preparation of the present invention is characterized by having a pH of less than about 7.3, preferably less than 7.0. It has been found that neutral to acidic pH levels improve the stability of the complex, and that the complex can be preserved by lyophilization in the presence of the excipient protein.

The excipient is preferably a pharmaceutically acceptable protein, such as human serum albumin and/or gelatin. The presence of the excipient permits the preparation to be diluted to useful dosage units while maintaining the solution stability of the neurotoxin/protein complex. The excipient also helps preserve the solubility and activity of the complex upon lyophilization and reconstitution of the composition.

A method for treating movement disorders characterized by uncontrolled muscle spasm using the pharmaceutical preparation is also the subject of the present invention. The treatment involves parenteral local administration of an effective dose of the present preparation directly to the afflicted muscle or muscles. The neurotoxin complex temporarily interrupts or lessens the neural connection between the muscle and nerve endings, thereby relieving the involuntary contraction of the muscle. Disorders which can be treated using the present preparation include, for example, blepharospasm, hemifacial spasm, spasmodic torticollis, spasmodic dysphonia, regional hand dystonias, and muscle hypertrophy.

DETAILED DESCRIPTION OF THE INVENTION

The pharmaceutical preparation of the present invention comprises a stable complex of purified botulinum toxin and non-toxic botulinum-derived proteins, together with an excipient. The composition is useful for treating spastic and/or contractile muscle disorders characterized by uncontrolled muscle spasm or hyperactivity.

The botulinum toxin used in the present composition preferably is a serotype B toxin derived from *Clostridium botulinum* (*C. botulinum*). The neurotoxin is a protein having a molecular weight of approximately 150,000 daltons. The active form of the toxin exists as a dichain molecule consisting of a light chain (~50,000 daltons) and a heavy chain (~100,000 daltons) linked by one or more disulfide bonds. Type B neurotoxin derived from the *C. botulinum* strain Okra B is particularly preferred. *C. botulinum* Okra B is available from various research groups and from the American Type Culture Collection as ATCC NO. 55323.

The botulinum-derived proteins which form a component of the complex with the neurotoxin comprise a red blood cell agglutinating factor which is coexpressed with the neurotoxin by *C. botulinum*. The proteins form a stable complex with the neurotoxin. One or more proteins may be associated with the neurotoxin molecule. A preferred complex formed from Type B neurotoxin and at least one protein has a molecular weight of about 300 KD (the M complex). Another preferred complex formed from type B neurotoxin and at least two proteins has a molecular weight of about 450 KD (the L complex). These complexes are preferred due their superior stability and potency compared to the non-complexed neurotoxin. The specific toxicities of the L and M complexes are about $4.0 \times 10^7$ to $4.8 \times 10^7$ mouse $LD_{50}$ per mg nitrogen (N) and about $8.8 \times 10^7$ to $9.6 \times 10^7$ mouse $LD_{50}$ per mg N, respectively. Type B toxin as purified from *C. botulinum* generally occurs as a mixture of L and M complexes.

An excipient preferably is added to the purified preparation, particularly during dilution and lyophilization. The term excipient as used herein refers to a pharmaceutically inert substance which is added to a pharmaceutical preparation as a vehicle or stabilizer. In the present case, a protein excipient such as human serum albumin (HSA) or gelatin is preferred.

The pharmaceutical preparation preferably has a pH of 7.3 or less, more preferably 7.0 or less. The use of acidic pH levels improves the stability of the toxin complex during and after dilution and helps to maintain the activity of the toxin complex upon lyophilization and subsequent reconstitution. It has been found that pH levels above 7.0 may cause the complex to dissociate, with subsequent loss of activity upon lyophilization.

The present composition can be prepared according to the following general procedure. *C. botulinum* bacteria which express the type B neurotoxin and the associated agglutinating proteins are grown to confluence using art-recognized techniques for culturing these bacteria. The neurotoxin-protein complex is released by the bacteria into the culture medium, from which it can be precipitated, for example, by lowering the pH to about 3.5 or less. The precipitate containing the neurotoxin complex then is separated from the culture medium. The toxin is extracted from the first precipitate by raising the pH to approximately 6.5 and stirring at ambient temperature in the presence of $CaCl_2$. The undissolved material is removed by centrifugation. The toxin in the supernatant is then reprecipitated by addition of hydrochloric acid (HCl) to pH 3.7. The second precipitate is collected by centrifugation, dissolved in 50 mM sodium citrate, pH 5.5, and exhaustively dialyzed against the same. Other acidic buffers may be used in lieu of sodium citrate. The dialyzed toxin complex is chromatographed by anion exchange chromatography at pH 5.5 using an amine-functional substrate such as DEAE-Sephadex™, for example. The unbound fraction contains the complex. The toxin complexes are precipitated with ammonium sulfate, and the precipitate is pelleted (e.g., by centrifugation), and can be further purified, if desired, by dialysis and chromatography. The resulting material is a highly concentrated, non-crystalline complex of highly pure Type B neurotoxin with its associated proteins which is substantially free of pyrogens or procaryotic proteins.

To make the pharmaceutical preparation of the present invention, the purified complex is admixed with an excipient and with a sterile diluent to dilute the toxin complex to useable dosage levels. The presence of the excipient helps to maintain the stability of the complex during and after dilution.

The diluent can be any pharmaceutically acceptable material which will not adversely affect the stability of the complex, preferably water. In a preferred embodiment of the present invention, the pH of the toxin solution is adjusted to a neutral to acidic pH, preferably less than 7.0. This can be accomplished using an acid such as hydrochloric acid, for example. Lower pH levels provide better stability during handling of the toxin complex, and permit recovery of higher levels of activity after drying and subsequent reconstitution. Between 90–100% recovery of toxin activity has been obtained following lyophilization at pH 5.0 using the present process. The results indicate that drying at pH 6.4 (the pH of commercially available HSA) recovers ≧75% of the activity.

The preparation containing the neurotoxin complex and the excipient can be dried for storage and/or shipping, if desired, and subsequently reconstituted. Drying is preferably accomplished by lyophilization. Lyophilization, or freeze-drying, is carried out by flash freezing the toxin complex in sterile vials and subliming the water present in the preparation under vacuum. The lyophilized product can be reconstituted with water, saline or standard phosphate buffer, for example, and the pH adjusted to the physiological range of 7.3 to 7.4 prior to injection.

The excipient is preferably used at a concentration sufficient to provide solution stability to the complex during and after dilution and to retain the desired activity level of the complex upon lyophilization and reconstitution. The excipient also ensures that the toxin does not adhere to glass. The concentration needed to accomplish these goals will depend in part upon which excipient is used. A concentration of from about 0.1 mg to about 1.0 mg of excipient per 100 units (U, measured as mouse $LD_{50}$) of the complex will be sufficient for most formulations. For example, a concentration of about 0.9 mg of human serum albumin (HSA) per vial containing 100 U of the complex provides stability to the toxin complex during dilution and upon lyophilization and reconstitution of the composition. The toxin complex is particularly susceptible to denaturation and inactivation when in a very dilute solution in the absence of an excipient.

Sterilization of the toxin by filtration prior to filling of the vials and lyophilization is preferred to ensure a safe product that will remain sterile.

The pharmaceutical composition of the present invention can be administered to an individual suffering from a spastic muscle disorder in order to temporarily relieve the spastic contraction of the afflicted muscle(s). Although the type B complex interrupts involuntary muscle contraction, it can permit voluntary muscle contraction in the treated muscles. In one embodiment, the treatment involves injecting the pharmaceutical composition directly into the muscle using, for example, a fine gauge teflon-coated needle under electromyographic control. A sufficient dose of the toxin acts on striated muscle to block release of the acetylcholine neurotransmitter from the presynaptic membrane. This results in effective denervation of the muscle in regions contacted by the toxin. The toxin causes an increase in post-synaptic acetylcholinesterase activity and an increase in the population of acetylcholine receptors; effects which occur as a characteristic physiological response to denervation. After a period of days, the axon terminals develop sprouting, and over a period of several months, collateral motor axons establish new neuromuscular connections with the muscle fiber. As neuromuscular junctions are regenerated, the function of the muscle returns along with the spasmodic contractions symptomatic of the disease. The treatment then must be repeated.

The dosage of the present composition which is administered for any given disease depends on the weight of the patient, and on the muscle group under treatment. It will generally be less than about 1000 U per dose, where U is defined as the $LD_{50}$ for a white mouse. One mouse $LD_{50}$ is deemed to be equal to one U. A dose in a particular instance can be determined empirically starting with very low doses and increasing the dose in accordance with observation and experience. Since different individuals can respond in different ways to the treatment, a dosage which is effective in one patient for a selected condition may not be identical to that required for another patient with the same condition. However, treatment protocols for type A toxin can provide some guidelines. In general, low doses are first administered and the effects determined. The doses are increased in small increments (i.e., titrated) until a desired effect is obtained with minimal negative side effects. A method for standardizing botulinum neurotoxins and for preparing uniquely standardized doses for clinical use is described in U.S. patent application Ser. No. 07/570,395, now U.S. Pat. No. 5,183,462, entitled "Controlled Administration of Chemodenervating Pharmaceuticals", the teachings of which are incorporated herein by reference.

A dosage of a few U up to about 500 to 1000 U can be used to achieve the desired therapeutic effect. Preferred dosage limits are less than about 500 U, preferably less than 300 U. Example 1 sets out a method for determining the activity of the type B neurotoxin complex based on the mouse $LD_{50}$. The botulinum type B neurotoxin complex described herein produces chemical denervation at the neuromuscular junction which results in reversible inhibition of normal neurotransmitter release. The present pharmaceutical composition contains a highly pure and highly active type B complex which is effective in treating neuromuscular disorders characterized by spastic or hyperactive muscle activity. The present composition provides a stable, injectable formulation and a method of using it to treat individuals afflicted by these painful and debilitating disorders.

The invention is further illustrated by the following Exemplification, which is not intended to be limiting in any way.

EXEMPLIFICATION

A. Purification of Type B Complex form C. Botulinum Okra B.

Materials

TPGY: trypticase peptone, glucose, yeast extract:

5.0% trypticase peptone (BBL Microbiology Systems, Becton Dickinson and Co., Cockeysville, Md. 21030)

0.5% bacto peptone (Difco Labs, Detroit, Mich.)

0.4% D-glucose (Mallinckrodt, Paris, Ky.)

0.2% cysteine-HCl (Sigma Chemical, St. Louis, Mo.)

0.1% yeast extract (Difco); pH 7.4.

M's medium: 2.0% trypticase peptone (BBL),

0.75% bacto peptone (Difco),

0.5% D-glucose (Mallinckrodt)

1.0% yeast extract (Difco); pH 7.4

DEAE-Sephadex™ A-50 (Sigma)

Procedure

Figure 1:
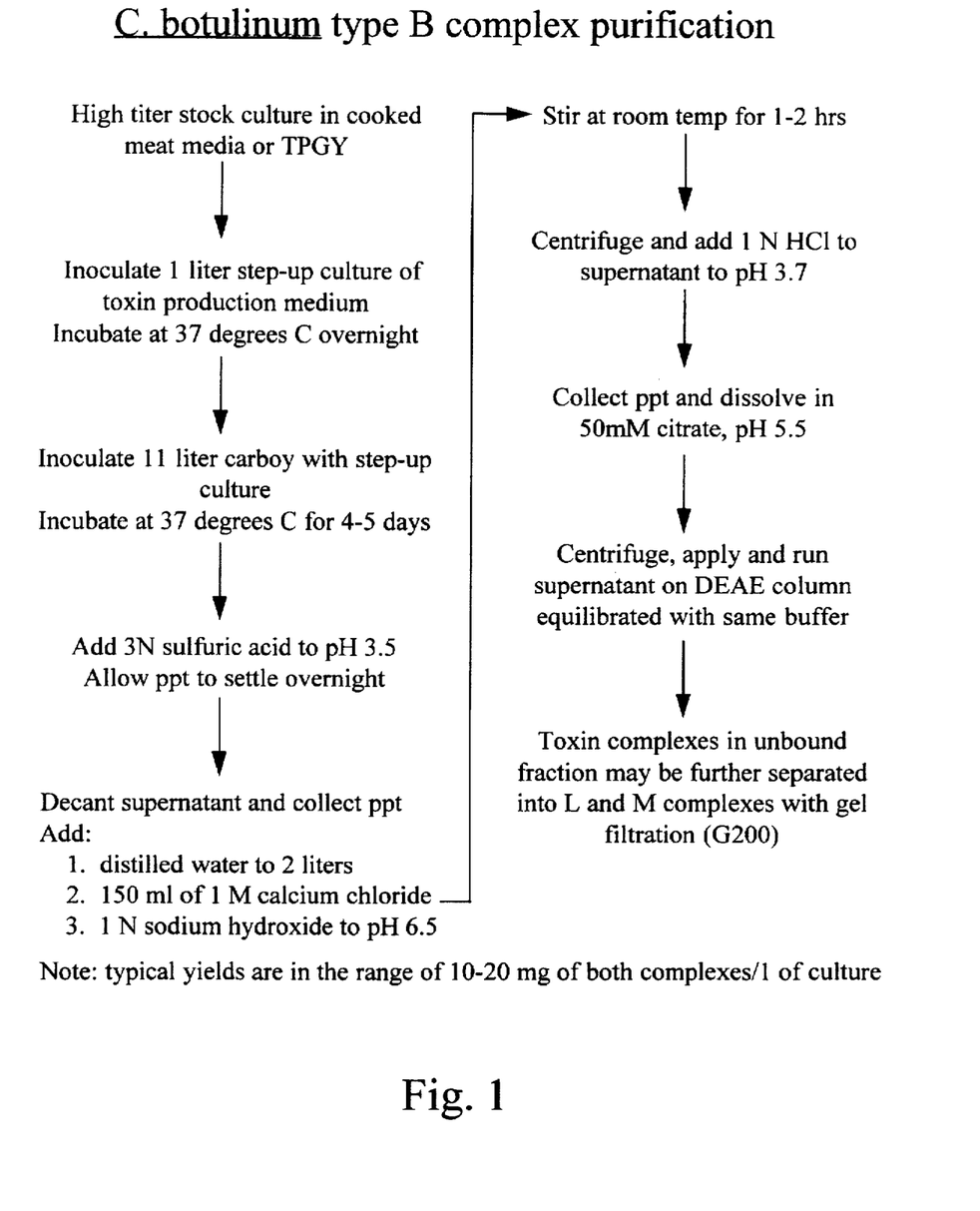
FIG. 1 is a flow chart illustrating the steps in a purification of C. botulinum type B complex.
Figure 2:
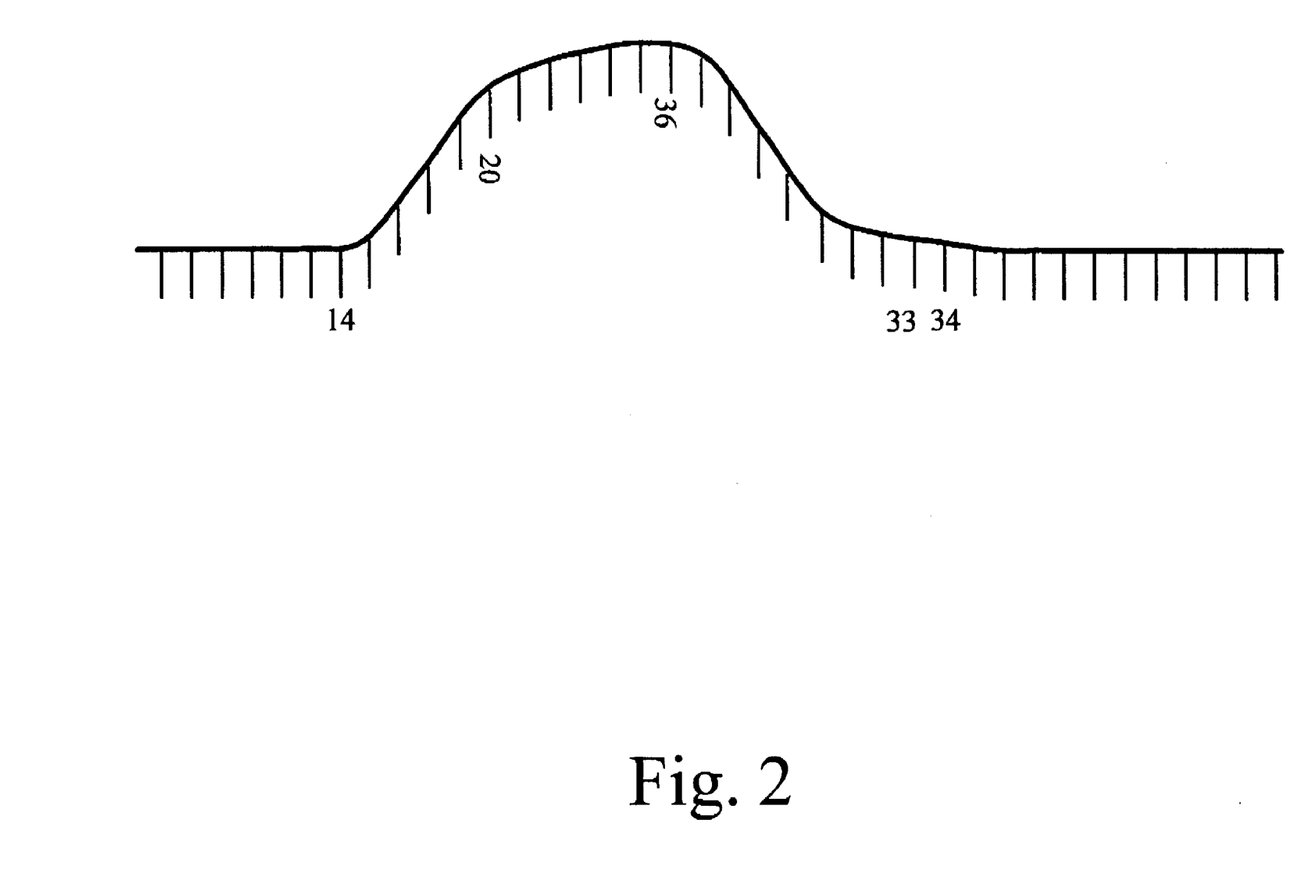
FIG. 2 is a graph showing the presence of the crude complex after chromatography on DEAE-Sephadex at pH 5.5 in 50 mM sodium citrate.
Figure 3:
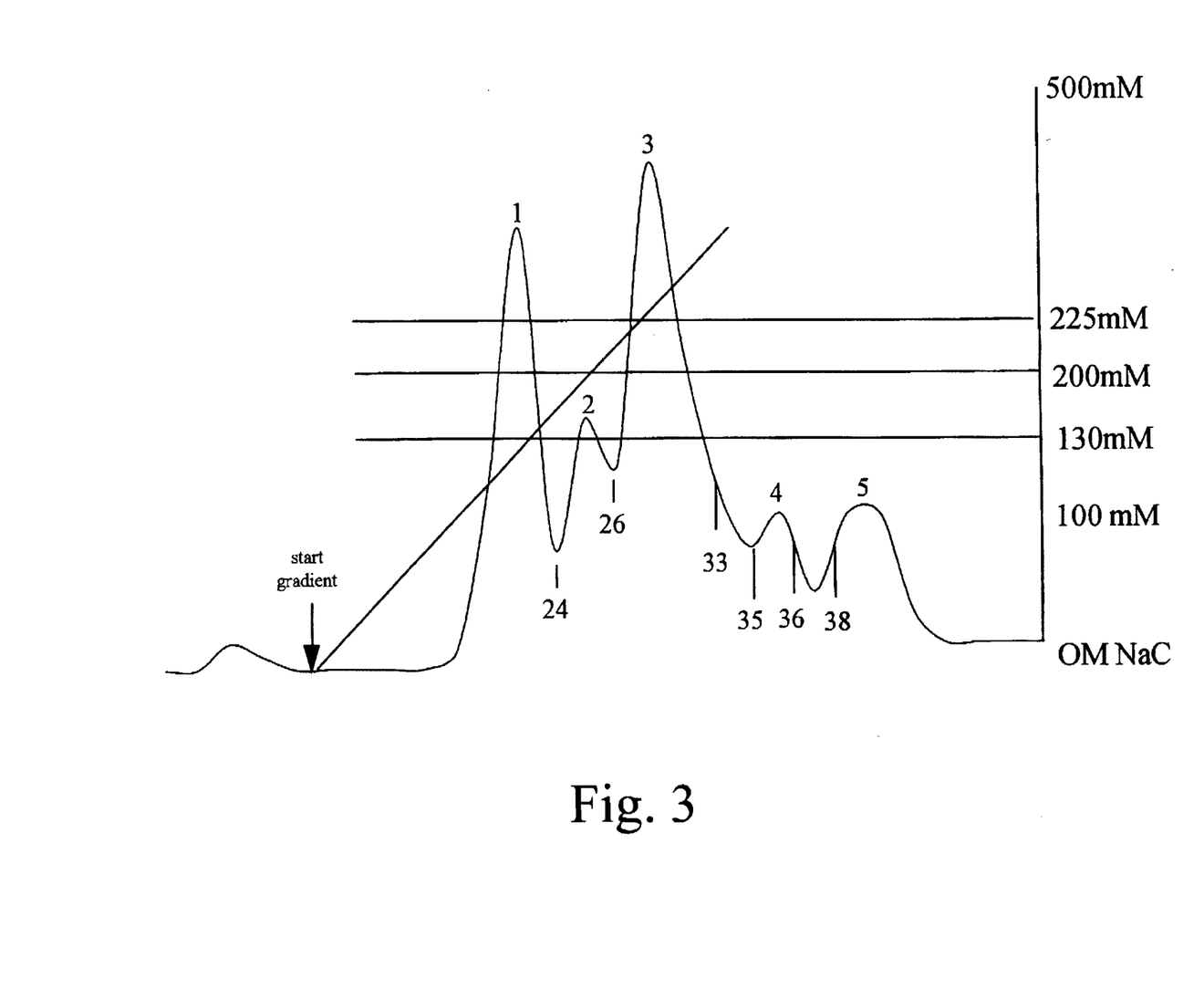
FIG. 3 is a graph showing chromatographic separation of the complexes on DEAE-Sephadex at pH 7.9 in 20 mM sodium phosphate with a 0 to 0.5M NaCl gradient, to pure neurotoxin and the associated nontoxic binding proteins. Peak 1 represents pure neurotoxin and peaks 2–5 are the associated nontoxic proteins.

A TPGY tube (10 ml) was inoculated with 0.5 ml of a frozen stock culture of C. botulinum Okra B (ATCC No 55323). The tube was incubated at 37° C. overnight. On the following day, a 1 liter step-up culture of M's medium was inoculated with about 10 ml of the TPGY tube and incubated at 37° C. After 24 hours, a 12 liter carboy of M's medium was inoculated with the step-up culture medium and incubated at 37° C. for about four days. After four days, the culture was brought to room temperature and the pH of the culture in the carboy was reduced to pH 3.5 with 3N $H_2SO_4$. The resulting precipitate was allowed to settle overnight at room temperature. The next day, the cleared supernatant was decanted and the precipitate allowed to settle further in a 2 liter graduated cylinder. The next day, the remaining supernatant was removed and 150 ml of 1.0M $CaCl_2$ was added with stirring. The total volume was increased to 2.0 liters with deionized water and the pH raised to 6.5 with 1N NaOH. The toxin solution was clarified by centrifugation, and the toxin reprecipitated by addition of 1N HCl to pH 3.7. The resulting precipitate was allowed to settle at room temperature overnight. The next day, the toxic precipitate was collected by centrifugation and dissolved in about 50 ml of 50 mM sodium citrate buffer, pH 5.5. The toxin was exhaustively dialyzed against the same buffer overnight. The dialyzed toxin was centrifuged and the supernatant chromatographed on a 1000 ml column of DEAE-Sephadex (Sigma) equilibrated with 50 mM sodium citrate, pH 5.5. The unbound fraction contained 135 mg protein as determined by measuring the optical density of the solution at $A_{278\ nm}$ (1.0 absorbance units at 278 nm=approximately 1.8 mg protein per ml) with a ratio of $OD_{260/278}$ of 0.51 (as shown in FIG. 2). The resulting complexes were non-crystalline and had an average specific toxicity of about $3\times10^7$ LD per mg. The toxin complexes were precipitated with ammonium sulfate to 60% saturation. When needed, approximately 30 mg of the ammonium sulfate precipitate was pelleted via centrifugation. The pellet was dissolved in 25 mM sodium phosphate, pH 7.9, and dialyzed against the same buffer. To confirm the presence of the toxin complex, the dialyzed material was then chromatographed on a 40 ml column of DEAE-Sephadex, pH 7.9. The toxin and associated non-toxic binding proteins of the complex were separated with a linear gradient of 0 to 0.5 M NaCl to separate the toxic and nontoxic proteins, as shown in FIG. 3. Peak 1 in FIG. 3 represents the purified neurotoxin, and Peaks 2 through 5 represent the nontoxic binding binding proteins.

B. Preparation of Botulinum Toxin Type B for Medical Use

A medical preparation of botulinum toxin was prepared using the purified toxin obtained as described above. The preparation had the following formulation:

C. botulinum type B toxin (non-crystalline suspension, dissolved to a concentration of 0.07 mg/ml in 25 mM sodium phosphate, pH 6.4);

Albumin (human, 25% solution USP), 0.72 ml; and

Sterile distilled water, 99.28 ml.

Determination of Biological Activity

The biological activity of the toxin was determined by mouse assay following dissolution and filtration.

The toxin required <3 hours to dissolve completely. the dissolution was performed at room temperature with occasional gentle mixing. Bubbles and violent agitation such as vortexing should be avoided as this causes denaturation.

The titer of this working stock was then determined by titration of the toxin via intraperitoneal injection in mice. This titration was done by serially diluting the toxin/HSA solution to extinction in 30 mM phosphate, 0.2% gelatin, pH 6.2 (gel-phosphate), and injecting white mice weighing 18–22 g intraperitoneally (IP) with 0.5 ml of each dilution. The final dilution which kills in 48–72 hours is then assumed to represent 2 mouse $LD_{50}$/ml (1 mouse lethal dose/0.5 ml). From this dilution, the number of $LD_{50}$/ml in the working stock can be calculated. The working stock is then diluted to 1,000 $LD_{50}$/ml in the same sterile 9.0 mg/ml HSA. The stock toxin solution was stored at 4° C.

Each of four to six mice were injected IP with 0.5 ml of appropriate dilutions to reach an endpoint. The dilution which killed 50% of the number of mice injected was then considered to represent $1LD_{50}$/0.5ml or 2 $LD_{50}$/ml. From this information, the titer of the original working stock was calculated and the appropriate dilutions made to obtain a solution with 200 $LD_{50}$/ml. Aliquots of 0.5 ml each were then delivered aseptically into sterile vials and the vials themselves lyophilized and sealed under nitrogen. The titer of the vials after lyophilization was determined by sampling an appropriate number.

For assay, the vials containing about 100 $LD_{50}$ were reconstituted by adding 1.0 ml of sterile water or saline to each vial being tested. The toxin and HSA were allowed to redissolve for at least 15 min at room temperature with gentle inversion to mix. The contents were then serially diluted as follows:

1:20 (100 µl of the reconstituted toxin in 1990 µl of gel-phosphate),

1:30 (66.7 µl of the reconstituted toxin into 1933.3 µl of gel-phosphate),

1:40 (50 µl of the reconstituted toxin into 1950 µl of gel-phosphate),

1:50 (40 µl of the reconstituted toxin into 1960 µl of gel-phosphate),

1:60 (33.3 µl of the reconstituted toxin into 1967.3 µl of gel-phosphate).

Each of three mice then were injected IP with 0.5 ml of each of the above dilutions and observed for 48–72 hrs. The endpoint as calculated from above was 100 $LD_{50}$/vial±20% before the batch was used.

C. Histochemical Effects of Botulinum B Toxin In Rabbits
Methods and Materials

The type B toxin used in these experiments was prepared from *C. botulinum* CDC culture 208 ("bean strain"—origin British culture collection, NCTC-7273). This organism provided the source for the type B toxoid preparation used in formulating the pentavalent vaccine.

The culture media consisted of 15 grams of trypticase (BBL Microbiology Systems) with 5 grams of yeast extract diluted in quantity sufficient to form 1,000 ml with normal saline. The pH was adjusted to 7.2 with sodium hydroxide (solution A). Another solution consisting of 20% glucose was autoclaved for 15 min at 121° C. (solution B). 10 ml of solution A was placed in 200 ml of solution B (solution C). A 24 hour culture of the organism was made with CMG media (BBL Microbiology Systems). 5 ml of the CMG—botulinum B toxin culture were used to inoculate solution C. Toxicity determinations were made over 3 days:

1 day . . . 10,000 Mouse $LD_{50}$/ml 2 day . . . 100,000 Mouse $LD_{50}$/ml 3 day . . . 100,000 Mouse $LD_{50}$/ml 1U=one $LD_{50}$ for white mouse.

3N sulfuric acid was added to the flasks after 3 days which develops the "mud", a suspension with stable biologic Type B toxin activity. This preparation was diluted with normal saline containing 5% glycerin, and 5% gelatin in acetate buffer adjusted to a pH of 4.7.

Muscle Histopathology:

Specimens taken from longissimus dorsi of 2–3 kg albino rabbits were immediately placed in cold (4° C.) formol-calcium (Baker's solution) and fixed for 6–12 hours at 4° C. Muscle specimens were then cryoprotected in gum sucrose solution for 3 hours. The muscle was oriented both in cross and longitudinal plane on a specimen chuck in OCT compound (Tissue Tek) and frozen in a cryostat. Cut tissue sections (10 µm) were adhered to gel coated slides, air dried for 2 minutes, and subsequently stained for acetycholinesterase activity (Geneser-Jensen and Blackstad, 1971). Enzyme histochemistry for myofibrillary ATPase activity (Brooke, Kaiser, (1969); Dubowitz and Brooke, *In: Muscle Biopsy: A Modern Approach*, J. N. Walton (ed.), W. B. Saunders Co. Ltd., London (1973)) and NADH activity (Scarpelli, Hess, Pearse, (1958); Dubowitz and Brooke, ibid.) was conducted on the specimens. Sections for acetylcholinesterase activity were incubated in a solution containing 13 ml of maleic buffer (1.96 g maleic acid, 0.8 g NaOH, 10.8 ml 1N NaOH, 200 ml distilled water), 10 mg acetylthiocholine iodide, 2 ml 0.03M cupric sulfate, 1 ml 0.1 sodium citrate, and 0.5M potassium ferricyanide for 1 hour at 37° C. Contiguous cryostat sections were stained either with hematoxylin and eosin or with Gomori trichrome stain to assess normal tissue morphology.

Alternativly, fresh skeletal muscle tissue was flash frozen in isopentane, and cooled to −160° C. using liquid nitrogen. Serial cut sections (10 µm) were stained with hematoxylin and eosin or trichrome to identify any tissue alterations. Enzyme histochemistry for acetylcholinesterase activity was used to quantify endplate structures and assess for denervation.

Histologic measurements were made with the Bioquant II system. Fiber size variation comparisons were generated using standard deviation and variance values counted from at least 200 fiber diameters. Also, a F ratio test was conducted to compare fiber size variability.

Results:
a. Five weeks after point injection of botulinum B toxin: (dose=15 U/kg)

Using the fiber size variability analysis as an indication of denervation, a marked degree of fiber size variability was demonstrated at the injection site 5 weeks after the injection of botulinum B toxin (fiber size diameter median=44.4 microns, variance=493, standard deviation=22.2). When compared to untreated control values (fiber size diameter average=37.95, variance=78.6, standard deviation=8.9), the fiber size variation was significantly greater than the controls (F ratio=4.32 P<0.01).

When comparing a muscle biopsy 3.0 cm from the injection point, there appeared to be a significant diminution in fiber size variability (median fiber diameter=58, variance=278, standard deviation=16.4). Fiber Size variability at three centimeters was significantly different from the injection point (F ratio=1.77, P<0.05), indicating regional denervation was more pronounced at the injection site than at three centimeters. Fiber size variability at 3.0 cm was, however, still significantly greater than fiber variability within control specimens (F ratio=2.4, p<0.01) indicating a denervation process even at this distance from the point injection.

Additionally, the spread of cholinesterase was most prominent at the injection site. At three centimeters from the injection site, there was a substantial diminution of acetylcholinesterase spread approaching normal intensity.

In control specimens, myofibrillary ATPase activity at pH 9.4 demonstrated type 1 and type 2 fibers. The number or percent ratio of type1/type2 fibers was 3.5% of the total. Type 1 fibers were evenly distributed throughout the muscle specimens in the saline injected control tissue. At the injection site there was marked variation of muscle fiber size effecting both fiber types. The pattern of fiber typing was altered in that there was now small groups or type 1 fibers, suggesting denervation and renovation. The ratio of type1/type2 fibers increased significantly with type 1 fibers representing 22% of the total population. Distally, 3.0 cm away from the injection site, there was much less fiber size variability. The percentage of type 1 fibers was reduced (10.7% of the total), although still not normal.

The NADH activity equally demonstrated alterations in the fiber size as well as the fiber typing. In addition, the method identified changes in the intermyofibrillary network consistent with denervation at the injection sites.

b. Fourteen weeks after point injecting of botulinum toxin B

There was significantly less acetycholinesterase staining when comparing the injection site at fourteen weeks versus five weeks. There were minimal differences in acetylcholinesterase activity at fourteen weeks compared to controls. Fiber size variability appeared not to be significantly different from control variability 14 weeks after injection, (average diameter=29.5 microns, variance=75.7, standard deviation=8.7, F ratio=0.7, P=NS).

Furthermore, there was no difference in fiber size variability or acetylcholinesterase staining pattern comparing the injection site with muscle tissue 4 cm from the injection after 13 weeks (fiber diameter=28.1, variance=54, s =7.4, F ratio–0.47, P=NS).

In summary, at 14 weeks both acetylcholinesterase and fiber size analysis did not appear to indicate significant denervation.

c. Botulinum A toxin diffusion gradient data after 5 weeks (Dose=2–3 U/kg)

There was considerable fiber size variation at the site of injection associated with the spread of acetylcholinesterase staining on muscle fibers in 3 animals studied (median diameter=27.3 microns, s=24.55, v=212, F ratio=2.5, P<0.01). At 15 mm from the injection site, similar fiber size variability and cholinesterase spread were noted (median diameter=30.7, s=12.9, v=166, F=1.98, p<0.01). At 40 mm there was considerable contraction of the acetylcholinesterase staining pattern as well as more uniform muscle fiber diameter sizes (median diameter=24.9, s=9.7, v=93, F=1.11, P=NS). At 45 mm, the acetylcholinesterase staining pattern and muscle fiber size variations were similar to controls (median diameter=30.6, s=6.4, v=41, F=0.49, P=NS).

d. Control muscle fiber diameter sizes and acetylcholinesterase staining pattern over the length of the longissimus dorsi.

Table 1 outlines control values for fiber size variability and acetylcholinesterase staining pattern at same saline injection site and 15 mm intervals.

TABLE 1

| Distance from Point Injection | Fiber Diameter | Variability | Cholinesterase Staining Pattern |
|---|---|---|---|
| Injection point | 37.2 | v = 84 | focal |
| 15 mm | 45 | v = 68 | focal |
| 30 mm | 31.9 | v = 35 | focal |
| 45 mm | 28.5 | v = 70.1 | focal |
| 60 mm | 41 | v = 65 | focal |

Note: The number or percent ratio of type 1/type 2 fibers was 3.5% of the total in control specimens.

The results demonstrate that type B toxin is capable of producing regional denervation from a point injection and has a reversability similar to type A toxin. Therefore, the regional denervation effect that has been pharmacologically useful with the A toxin can be duplicated by application of the B toxin.

Equivalents

Those skilled in the art will be able to ascertain, using no more than routine experimentation, several equivalents to the specific embodiments described herein. Such equivalents are intended to be encompassed by the following claims.

What is claimed is:

1. A pharmaceutical preparation for use in inducing local, partial, titratable, muscle denervation in a patient, the preparation comprising:

a frozen, dried sodium chloride-free preparation comprising C. botulinum type B neurotoxin complexed with botulinum-derived stabilizing proteins, the complex having a molecular weight as determined by gel filtration chromatography of from about 300 KD to about 450 KD, in admixture with a pharmaceutically acceptable protein excipient for maintaining the stability of the complex at concentrations of $10^4$ mouse $LD_{50}$ units per milliliter or less, which, when reconstituted in aqueous solution, retains at least 75% of its toxic activity.

2. The pharmaceutical preparation of claim 1 characterized as having a pH between 5.0 and 7.3 when reconstituted.

3. The pharmaceutical preparation of claim 1 which, when reconstituted retains at least 90% of its toxic activity.

4. The pharmaceutical preparation of claim 1 wherein the protein excipient is selected from the group consisting of albumin and gelatin.

5. The pharmaceutical preparation of claim 1 wherein at least one of said stabilizing proteins comprises a red blood cell agglutinating factor coexpressed with the neurotoxin by *C. botulinum*.

6. The pharmaceutical preparation of claim 1 substantially free of bacterial proteins other than said neurotoxin and stabilizing proteins.

7. A method of selectively, partially, temporarily, chemically denervating a volume of muscle in a mammal, the method comprising the steps of:
   reconstituting the frozen, dried preparation of claim 1 to form a toxically active aqueous solution;
   injecting into a point within said muscle volume a dose of the reconstituted composition sufficient to reduce involuntary contraction thereof while permitting continuing voluntary contraction; and
   permitting said dose to diffuse throughout said muscle volume to induce partial denervation thereof.

8. The method of claim 7 further comprising:
   injecting individual doses of said composition into sites spaced apart within said predetermined volume of muscle, the spatial relationship of the sites being sufficient to at least partially denervate the entirety of said volume.

9. The method of claim 7 wherein said volume of muscle comprises a single muscle, the method comprising injecting a unit dose of said pharmaceutical, into an innervating zone of said muscle, and permitting said dose to diffuse through said innervating zone to induce partial denervation of the entirety of said muscle.

10. A method of decreasing spasm and involuntary contraction in a muscle of a patient induced by pathologic neural stimulation, the method comprising the steps of reconstituting the frozen, dried preparation of claim 1 and injecting into at least a portion of an innervation zone of the muscle the reconstituted preparation in an amount sufficient to diminish spasm and involuntary contraction while permitting voluntary muscle stimulation.

11. A method of decreasing tremor, rigidity, or spasticity in a muscle of a patient, the method comprising the steps of reconstituting the frozen, dried preparation of claim 1 and injecting into at least a portion of an innervation zone of the muscle the reconstituted preparation in an amount sufficient to diminish tremor, rigidity, or spasticity while permitting voluntary muscle stimulation.

12. A frozen, dried, sodium-chloride-free botulinum toxin preparation which, when reconstituted in aqueous media, retains greater than 75% of its regional chemodenervating activity.

13. The toxin preparation of claim 12 which, when reconstituted in aqueous media, retains greater than 90% of its activity.

14. A method of preparing a storage stabilized botulinum toxin pharmaceutical preparation comprising the step of:
   freeze drying a purified toxin in a sodium chloride-free aqueous solution having a pH between 5.0 and 7.3, and containing a stabilizing protein as an excipient.

15. The method of claim 14 wherein said aqueous solution comprises phosphate buffer.

16. The preparation of claim 12 which, prior to being frozen and dried, is dialyzed to remove salts.

* * * * *

UNITED STATES PATENT AND TRADEMARK OFFICE
CERTIFICATE OF CORRECTION

| | |
|---|---|
| PATENT NO. | : 5,696,077 |
| DATED | : December 9, 1997 |
| INVENTOR(S) | : Eric A. Johnson et al. |

It is certified that error appears in the above-identified patent and that said Letters Patent is hereby corrected as shown below:

<u>Title page,</u>
Item [63], Related U.S. Application Data, "[63] Continuation of Ser. No. 08/140,328, Oct. 20, 1993, abandoned, which is a continuation of Ser. No. 07/903,207, Jun. 23, 1992, abandoned."

Signed and Sealed this

Twentieth Day of July, 2004

JON W. DUDAS
*Acting Director of the United States Patent and Trademark Office*